United States Patent [19]

Bach et al.

[11] 3,959,288

[45] May 25, 1976

[54] 8-OXYMETHYLERGOLINES AND PROCESS THEREFOR

[75] Inventors: Nicholas J. Bach; Edmund C. Kornfeld, both of Indianapolis, Ind.

[73] Assignee: Eli Lilly and Company, Indianapolis, Ind.

[22] Filed: Dec. 13, 1974

[21] Appl. No.: 532,333

[52] U.S. Cl. .............................. 260/285.5; 424/261
[51] Int. Cl.² ..................................... C07D 457/02
[58] Field of Search ................................. 260/285.5

[56] References Cited
UNITED STATES PATENTS

| | | | |
|---|---|---|---|
| 3,709,891 | 1/1973 | Eich et al. | 260/285.5 |
| 3,732,231 | 5/1973 | Semonsky et al. | 260/285.5 |
| 3,901,894 | 8/1975 | Kornfeld et al. | 260/285.5 |

OTHER PUBLICATIONS

Zikan et al.; Coll. Czech. Chem. Comm.; Vol. 39, pp. 614–616, (1974).

*Primary Examiner*—Alton D. Rollins
*Assistant Examiner*—Mary Vaughn
*Attorney, Agent, or Firm*—Charles W. Ashbrook; Everet F. Smith

[57] ABSTRACT

6-methyl-8-alkoxymethylergolines are prepared by reaction of a 6-methyl-8-(substituted)methylergoline with a benzyl quaternary ammonium alkoxide. 6-Methyl-8-phenoxymethylergolines are prepared by reaction of an 8-(substituted)-methylergoline with phenol in the presence of strong base. The new 8-oxymethylergolines of this invention are useful as prolactin inhibitors.

12 Claims, No Drawings

8-OXYMETHYLERGOLINES AND PROCESS THEREFOR

BACKGROUND OF THE INVENTION

Numerous naturally occuring and semi-synthetic ergot alkaloid compounds have been shown to possess a wide variety of useful pharmacological activities. Several ergot alkaloids and their derivatives have demonstrated an ability to inhibit prolactin secretion, and consequently such compounds have shown a potential usefulness in treating prolactindependent conditions in which an undesirable excess of prolactin is present. Certain ergot compounds have thus been used in lactating rats and in rats bearing mammary tumors. Ergocornine and ergocryptine, for instance, inhibited mammary tumor growth and development in rats, as demonstrated by Cassell et al., *Cancer Res.*, 31, 1051 (1971).

The ergot alkaloids and their derivatives are characterized as being a group of nitrogen-containing compounds having the following basic tetracyclic structure

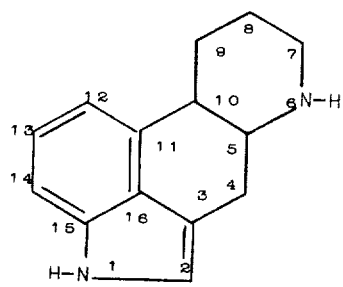

I

Compounds having the above general structure are referred to as ergolines. The term "ergoline" is used throughout the present specification and claims to include compounds having a 9,10-double bond, as well as the 9,10-saturated compounds exemplified by the above structure. The naturally occuring ergolines and most of the ergolines produced by partial or total synthesis are 6-methylergolines. The known ergolines differ from one another primarily in the nature of the side chain attached in the 8-position, which difference can dramatically affect the biological activity of the respective compound. For example, D-6-methyl-8-carboxy-$\Delta^9$-ergoline, a 9-ergolene known by the trivial name lysergic acid, has little biological activity. In contrast, the simple diethylamide of lysergic acid is an exceptionally potent central nervous system stimulant.

Several important ergolines are characterized as being 8-methyl, 8-hydroxymethyl, and 8-(substituted)-methylergolines. For example, elymoclavine is 6-methyl-8-hydroxymethyl-8-ergolene and is a potent prolactin inhibitor. D-6-methyl-8-cyanomethylergoline, prepared by Semonsky and coworkers and described in *Coll. Czech. Chem. Commun.*, 33, 577 (1968), was found to be useful in preventing pregnancy in rats, as detailed in *Nature*, 221, 66 (1969), and U.S. Pat. No. 3,732,231.

To date, only one 8-alkoxymethylergoline has been prepared and isolated. In particular, Zikan and Semonsky prepared D6-methyl-8-n-butoxymethylergoline by reaction of sodium butylate and the corresponding 8-chloromethylergoline. These workers reported that the reaction, when carried out with most sodium alcoholates, led primarily to elimination of hydrochloric acid and provided the corresponding 8-methylenergoline derivative; see *Coll. Czech. Chem. Comm.* 39, 614 (1974). Indeed, reaction of D-6-methyl-8-chloromethylergoline with sodium methoxide under the conditions taught by Zikan and Semonsky, effected only elimination of the elements of hydrochloric acid, affording exclusively the corresponding 8-methylenergoline.

An object of this invention is to provide a process for preparing 8-alkoxymethylergolines with minimum elimination to give the 8-methylenergoline by-product. A further object of the invention is to provide hitherto unavailable 8-alkoxymethylergolines, in addition to other new ergolines.

SUMMARY OF THE INVENTION

This invention relates to a process for preparing 8-alkoxymethylergolines, and to novel 8-oxymethylergoline compounds. More particularly, this invention provides a process for preparing the compound having the general formula

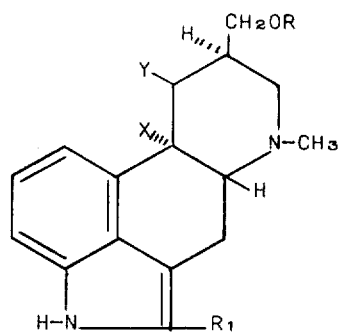

II in which X and Y both are hydrogen or, taken together, form a double bond; R is $C_1$–$C_4$ alkyl; and $R_1$ is hydrogen, chlorine, or bromine; comprising reacting an 8-(substituted)methyl-ergoline with a benzyltrialkylammonium $C_1$–$C_4$ alkoxide.

This invention further provides new compounds of the formula

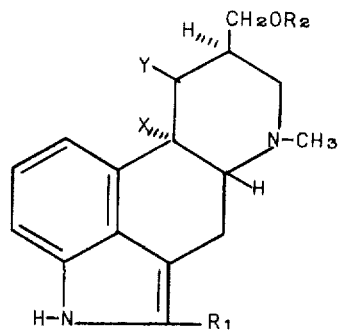

III in which $R_2$ is methyl or phenyl, and X, Y, and $R_1$ have the above-defined meanings. The pharmaceutically acceptable salts of the compounds having the above formula are included within the scope of this invention.

A preferred group of new ergolines provided by this invention have the above formula in which $R_1$ is hydrogen.

DETAILED DESCRIPTION OF THE INVENTION

This invention provides new ergot alkaloids and a novel process for preparing 8-alkoxymethylergolines. The compounds described hereinbelow are named according to accepted ergoline nomenclature. All of the compounds disclosed herein have an oxymethyl substituent in the 8β-position of the ergoline ring system, as evidenced in the above formula by the solid bonding line between C-8 of the ergoline ring system and the group designated by $CH_2OR$. The term "β" is to be understood and will be omitted hereinafter by way of simplification when naming the ergolines of this invention. Compounds having the above formula in which X and Y taken together form a double bond are referred to as $\Delta^9$-ergolines, or alternatively as 9-ergolenes, and will be hereinafter referred to as 9-ergolenes.

The compounds of this invention are tetracyclic nitrogen-containing bases, and typically exist as white crystalline solids. The compounds readily form non-toxic pharmaceutically acceptable acid addition salts with any of a number of inorganic and organic acids commonly used in the art to form pharmaceutically acceptable salts of bases. Typical inorganic acids useful in forming salts of this invention include hydrochloric acid, hydrobromic acid, hydroiodic acid, sulfuric acid, nitric acid, phosphoric acid, and related acids. Organic acids commonly used in salt formation include aliphatic mono- and dicarboxylic acids, aromatic acids, aliphatic and aromatic sulfonic acids, and the like. Specific examples of such acids include isobutyric acid, methanesulfonic acid, succinic acid, maleic acid, malonic acid, oxalic acid, benzoic acid, p-toluenesulfonic acid, 1-naphthalenesulfonic acid, and related acids. Pharmaceutically acceptable acid addition salts of ergoline bases are generally prepared by reaction of the ergoline free base with an equivalent amount of an acid, typically in a solvent such as diethyl ether, ethyl acetate, benzene, or the like. The acid addition salts are characteristically crystalline solids and can be isolated by filtration. Alternatively, an excess of acid can be added to a solution of the ergoline base. For example, a solution of an ergoline in ether can be saturated with hydrogen chloride gas or hydrogen bromide gas, thereby precipitating the corresponding acid addition salt, which can be collected by filtration.

In accordance with this invention, compounds having the above formula in which $R_2$ is phenyl are prepared by reacting an ergoline having a readily displaceable group attached to an 8-methyl substituent with an alkali metal salt of phenol, such as sodium phenoxide or lithium phenoxide.

"A readily displaceable group" refers herein to a leaving group which can easily be replaced by a nucleophile. Such groups are well known to those in the art and generally include halogen atoms such as bromine, chlorine, or iodine; oxonium ions; and particularly esters of sulfuric and sulfonic acids, for instance methanesulfonyloxy or p-toluenesulfonyloxy groups.

Typical ergolines having a readily displaceable group attached to the 8-methyl substituent include the methanesulfonyl ester or the p-toluenesulfonyl ester of an 8-hydroxymethylergoline. Specific examples of such ergolines suitably substituted with a readily displaceable group include D-6-methyl-8-(methanesulfonyloxy)methylergoline; 2-chloro-6-methyl-8-(p-toluenesulfonyloxy)methyl-9-ergolene; 2-bromo-6-methyl-8-(methanesulfonyloxy) and the like. The conversion of such ergolines to the corresponding 8-phenoxymethyl derivative is accomplished by commingling, in an organic solvent, an ergoline, for instance an 8-(methanesulfonyloxy)-methylergoline, with an alkali metal salt of phenol, for example sodium phenoxide, formed by reaction of sodium hydride with phenol. The alkali metal phenoxide is generally employed in an excessive amount ranging from about 5 to 20 molar excess. Typical solvents routinely used for the displacement reaction include amides such as hexamethylphosphortriamide or dimethylformamide; sulfoxides such as dimethyl sulfoxide or diisopropyl sulfoxide; and ethers such as dioxane or tetrahydrofuran. The reaction is generally carried out at a temperature in the range of about 30° to 150°C., and at this temperature the displacement reaction is substantially complete within about 15 minutes to 2 hours. The product, an 8-phenoxymethylergoline, is normally isolated by adding water to the reaction mixture and making the aqueous solution alkaline, for instance by adding a base such as sodium hydroxide, and subsequently extracting the water-insoluble product from the aqueous alkaline reaction mixture into a water-immiscible solvent, such as ethyl acetate, chloroform, diethyl ether, or the like. Evaporation of the solvent from the extracts affords the desired product, typically as a crystalline solid. The product can be further purified if desired by standard techniques such as recrystallization, chromatography, or the like. The compound so formed can be converted to a pharmaceutically acceptable acid addition salt by reaction with an acid, for instance maleic acid, hydrochloric acid, methanesulfonic acid, or the like.

Compounds having the above formula in which $R_2$ is methyl are prepared by the novel process provided by this invention. This process is applicable not only to the 8-methoxymethylergolines of this invention, but also to 8-alkoxymethylergolines in general, in which the alkoxy group is a $C_1$—$C_4$ alkyloxy group. Included among such $C_1$—$C_4$ alkyloxy groups are methoxy, ethoxy, n-propoxy, isopropoxy, n-butoxy, isobutoxy, and the like. These 8-alkoxymethyl derivatives can be prepared by the novel process of this invention without the concomitant formation of substantial amounts of 8-methylenergolines, which compounds represent major by-products, if not the sole product, in known reactions leading to the 8-alkoxymethylergolines, for instance the methods taught by Zikan and Semonsky, in *Coll. Czech. Chem. Comm.* 39, 614 (1974).

According to the novel process of this invention, an ergoline having a readily displaceable group attached to an 8-methyl substituent, especially a methanesulfonyl ester or a p-toluenesulfonyl ester of an 8-hydroxymethylergoline, is reacted with a benzyltrialkylammonium $C_1$–$C_4$ alkoxide. Examples of suitably substitued ergolines useful as starting materials in the present process include D-6-methyl-8-(methanesulfonyloxy)methylergoline, 2-bromo-6-methyl-8-(p-toluenesulfonyloxy)methyl-9-ergolene, 2-chloro-6-methyl-8-(methanesulfonyloxy)methyl-9-ergolene, and related ergolines. Examples of typical benzyltrialkylammonium alkoxides commonly used in the displacement reaction include benzyltrimethylammonium methoxide, benzyltriethylammonium ethoxide, benzyltriethylammonium n-propoxide, benzyltrimethylammonium n-butoxide, benzyldimethylethylammonium isobutoxide, and the like. Preferred benzyltrialkylammonium alkoxides are the benzyltrimethylammonium $C_1$-$C_4$ alkoxides. The process is generally carried out by commingling a suitably substituted ergoline and a benzyltrialkylammonium alkoxide in a non-aqueous solvent. The ergoline and the quaternary ammonium alkoxide are generally utilized in about equimolar amounts; however, excess amounts of the benzyltrialkylammonium alkoxide can be incorporated if desired, since the ergoline is the more expensive starting material. For example, an excess ranging from about 1 to 10 molar excess, or more, of quaternary ammonium alkoxide can be added to the reaction mixture if desired. Any of a number of common nonaqueous solvents can be utilized for the reaction, including lower alcohols such as methanol, ethanol, isopropanol, n-butanol, isobutanol, and the like; as well as ethers such as dioxane or tetrahydrofuran; amides such as dimethylformamide or hexamethylphosphortriamide; and aromatic hydrocarbons such as benzene, toluene, xylene, and the like. A lower alcohol is typically a preferred reaction solvent, and the particular alcohol selected often corresponds to the benzyltrialkylammonium alkoxide being used. For example, when a benzyltrialkylammonium methoxide is utilized, the preferred solvent is methanol. The displacement reaction between the suitably substituted ergoline and the benzyltrialkylammonium alkoxide is normally carried out at a temperature below about 150°C., for instance at a temperature between 0° and 135°C., preferably within the range of 30° to 100°C. When carried out at a temperature within the preferred temperature range, the reaction is substantially complete within about 20 to 100 hours; however, longer or shorter reaction times can be employed if desired. The product of the displacement reaction, an 8-alkoxymethylergoline, is normally isolated by adding water to the reaction mixture and extracting the product therefrom into any of a number of water-immiscible organic solvents, such as ethyl acetate, chloroform, diethyl ether, or the like. Evaporation of the solvent from the separated extract provides the desired 8-alkoxymethylergoline product, normally as a crystalline solid. Further purification of the compound can be accomplished by any of a number of routine methods, including recrystallization, chromatography, salt formation, and the like. When desired, the 8-alkoxymethylergoline can be converted to a non-toxic pharmaceutically acceptable acid addition salt by reaction with any of a number of acids commonly used for salt formation, for instance hydrochloric acid, maleic acid, sulfuric acid, methanesulfonic acid, and related acids.

Examples of 8-oxymethylergolines provided by the present invention include:

D-6-methyl-8-methoxymethylergoline methanesulfonate;

D-2-bromo-6-methyl-8-phenoxymethyl-9-ergolene;

D-2-chloro-6-methyl-8-methoxymethyl-9-ergolene hydrochloride;

D-2-bromo-6-methyl-8-methoxymethyl-9-ergolene hydroacetate; and

D-2-bromo-6-methyl-8-phenoxymethylergoline.

As hereinbefore indicated, the 8-oxymethylergolines provided by this invention possess a variety of pharmacological activities, and are especially useful as inhibitors of prolactin secretion. Consequently, the new ergolines of this invention are potentially useful in the treatment of various prolactin-dependent conditions wherein an excess of prolactin is undesirable, such as prolactin-dependent adenocarcinomas and prolactin-secreting pituitary tumors, postpartum lactation and galactorrhea.

In order to inhibit prolactin secretion, the compound of this invention, or pharmaceutically acceptable salts thereof, will be suitably admixed with diluents, excipients, or carriers, and formulated for convenient oral or parenteral administration to a subject. The compound will be administered in an amount varying from about 0.01 to 10 mg. per Kg. of mammalian body weight, generally from 1 to 4 times per day. Examples of diluents, excipients, and carriers routinely used in formulating the compounds of this invention include dextrose, sucrose, starch, talcum, magnesium stearate, and like substances routinely used in pharmacy. For oral administration, the compound of this invention, ideally as a pharmaceutically acceptable acid addition salt such as the methanesulfonate salt, is formulated with starches, sugars, talcum, and the like, and molded into tablets or encapsulated into empty telescoping gelatin capsules. Parenteral administration can be accomplished by a variety of routes including intravenous, intramuscular or intraperitoneal injection. Typical formulations suitable for parenteral administration include a compound of this invention in association with suitable diluents or carriers such as sodium chloride, sorbital, mannitol, magnesium aluminum sulfate, and the like, dissolved in a suitable solvent such as sterile water or saline solution.

The ability of the compounds of this invention to inhibit prolactin secretion was demonstrated by carrying out the following experiment.

Adult male rats of the Sprague-Dawley strain weighing about 200 g. were housed in an air-conditioned room with controlled lighting and fed lab chow and water ad libitum. Each rat received an intraperitoneal injection of 2.0 mg. of reserpine in aqueous suspension 18 hours before administration of the ergoline derivative in order to maintain prolactin levels uniformly elevated. The novel ergoline derivatives of this invention were dissolved in 10 percent aqueous ethanol at a concentration of 10 $\mu$g./ml., and were injected intraperitoneally into the male rats at a dose of 50 $\mu$g./kg. of body weight. Control rats were injected with an equal amount of 10 percent aqueous ethanol. The rats were killed by decapitation one hour following administration of the ergoline derivative, and the serum was collected. Aliquot portions of 150 $\mu$l of serum were assayed for prolactin content. The difference between the prolactin level of the treated rats and the prolactin level of the control rats, divided by the prolactin level of the control rats gives the percent inhibition of prolactin secretion attributable to the compounds of the present invention. As an example, D-6-methyl-8-methoxymethylergoline demonstrated 32 percent prolactin inhibition when tested according to the above described experiment.

The following detailed examples are set forth to more fully illustrate specific embodiments of the present invention. The examples should not, however, be construed as limiting the invention to the particular aspects presented therein.

EXAMPLE 1

D-6-Methyl-8-methoxymethylergoline

A suspension of 705 mg. of D-6-methyl-8-(methanesulfonyloxy)methylergoline in 50 ml. of methanol was stirred under a nitrogen atmosphere at 24°C. while 5 ml. of a 40 percent solution of benzyltrimethylammonium methoxide in methanol was added in one portion. The reaction mixture was stirred at 24°C. for 2 hours and then heated at reflux for 70 hours. The reaction mixture was added to 50 ml. of water, and the product was extracted from the aqueous mixture into chloroform. The combined organic extracts were washed, dried, and the solvent was removed therefrom under reduced pressure, leaving an oil. The oil was applied to a chromatographic column packed with 35 g. of florisil, and the column was eluted with chloroform containing from 2 to 5 percent methanol by volume. Eluate fractions shown to contain the desired product by thin layer chromatography were combined and the solvent was evaporated therefrom under reduced pressure, affording the product as a foam. The foam was recrystallized from diethyl ether and hexane, affording D-6-methyl-8-methoxymethylergoline in 75 percent yield. M.P. 191°–192°C.

Analysis — Calc. for $C_{17}H_{22}N_2O$: Theory: C, 75.52; H, 8.20; N, 10.36. Found: C, 75.31; H, 8.00; N, 10.11.

EXAMPLE 2

D-6-methyl-8-phenoxymethylergoline

A solution of 685 mg. of D-6-methyl-8-(methanesulfonyloxy)methylergoline in 50 ml. of dimethylformamide was added dropwise over 5 minutes to a stirred solution of 2 g. of phenol and 475 mg. of sodium hydride in 50 ml. of dimethyl formamide. The reaction mixture was heated at 100°C. under a nitrogen gas atmosphere for 30 minutes. The reaction mixture was cooled to room temperature, and aqueous potassium hydroxide was added to adjust the pH to 11. The aqueous alkaline reaction mixture was extracted several times with ethyl acetate, and the combined extracts were washed with water, dried, and the solvent was removed therefrom under reduced pressure, providing the product as an oil. The oil was chromatographed over 30 g. of florisil, eluting with chloroform containing from 2 to 5 percent ethyl acetate by volume. Eluate fractions shown to contain the desired product by thin layer chromatography were combined and the solvent was removed therefrom under reduced pressure, affording a foam. The foam was recrystallized from ethanol, affording D-6-methyl-8-phenoxymethylergoline as a white crystalline solid in 77 percent yield. M.P. 217°–219°C.

Analysis — Calc. for $C_{22}H_{24}N_2O$. Theory: C, 79.48; H, 7.28; N, 8.43. Found: C, 79.26; H, 7.03; N, 8.22.

EXAMPLE 3

6-Methyl-8-phenoxymethyl-9-ergolene

A solution of 4 g. of phenol in 75 ml. of dimethylformamide was cooled to 5°C. in an ice-water bath and stirred while 2 g. of a 50 percent solution of sodium hydride in mineral oil was added slowly in five portions over 10 minutes. The reaction mixture was stirred at 24°C. under a nitrogen atmosphere while a solution of 1.62 g. of 6-methyl-8-(methanesulfonyloxy)methyl-9-ergolene in 75 ml. of dimethylformamide was added dropwise over 15 minutes. The reaction mixture was stirred under nitrogen for 1 hour at 24°C. and then heated at reflux for 30 minutes. The reaction mixture was cooled to about 30°C. and added to 100 ml. of 5 percent aqueous potassium hydroxide solution. The aqueous alkaline solution was extracted several times with ethyl acetate, and the combined extracts were washed with water, dried, and the solvent was removed therefrom under reduced pressure, leaving an oily residue. The oil was chromatographed over 30 g. of florisil, eluting with chloroform containing from 2 to 5 percent of methanol by volume. Eluate fraction shown by thin layer chromatography to contain the desired product were combined and the solvent was evaporated under reduced pressure, providing a foam which was recrystallized from diethyl ether and hexane, affording 6-methyl-8-phenoxymethyl-9-ergolene. M.P. 178°–180°C.

Analysis — Calc. for $C_{22}H_{22}N_2O_4$. Theory: C, 79.97; H, 6.71; N, 8.48. Found: C, 79.76; H, 6.49; N, 8.27.

EXAMPLE 4

6-Methyl-8-phenoxymethylergoline maleate

A solution of 3.3 g. of 6-methyl-8-phenoxymethylergoline in 50 ml. of diethyl ether was stirred while a solution of 0.58 g. of maleic acid in 10 ml. of diethyl ether was added in one portion. After stirring for about 1 hour, the crystalline 6-methyl-8-phenoxymethylergoline maleate salt was collected by filtration.

EXAMPLE 5

6-Methyl-8-methoxymethyl-9-ergolene hydrochloride

Hydrogen chloride gas was bubbled into a solution of 6-methyl-8-methoxymethyl-9-ergolene in 50 ml. of diethyl ether. The crystalline 6-methyl-8-methoxy-9-ergolene hydrochloride salt was collected by filtration and dried.

We claim:
1. A compound of the formula

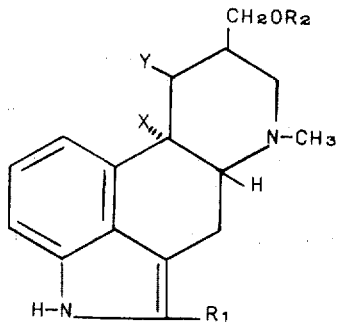

wherein:
X and Y both are hydrogen or, taken together, form a double bond;
$R_1$ is hydrogen, chlorine, or bromine;
$R_2$ is methyl or phenyl; and
the pharmaceutically acceptable acid addition salts thereof.

2. A compound of claim 1 wherein $R_2$ is phenyl.
3. A compound of claim 2 wherein $R_1$ is hydrogen.
4. The compound of claim 3 wherein X and Y are both hydrogen.
5. A compound of claim 1 wherein $R_2$ is methyl.
6. A compound of claim 5 wherein $R_1$ is hydrogen.
7. The compound of claim 6 wherein X and Y are both hydrogen.
8. The pharmaceutically acceptable acid addition salt of a compound of claim 1.
9. The process for preparing a compound having the formula

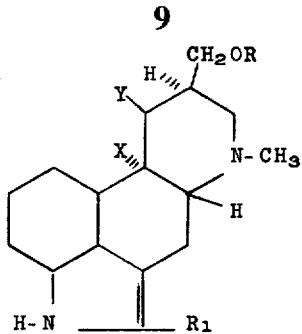

wherein:
X and Y both are hydrogen, or taken together, form a double bond;
$R_1$ is hydrogen, chlorine, or bromine;

and R is $C_1$–$C_4$ alkyl; comprising the step of reacting a benzyltrialkylammonium $C_1$–$C_4$ alkoxide with an ergoline having an 8-methyl substituent bearing a readily displaceable group.

10. The process according to claim 9 wherein the readily displaceable group is selected from the group consisting of methanesulfonyloxy and p-toluenesulfonyloxy.

11. The process according to claim 10 wherein the benzyltrialkylammonium alkoxide is a benzyltrimethylammonium $C_1$–$C_4$ alkoxide.

12. The process according to claim 11 wherein the benzyltrimethylammonium $C_1$–$C_4$ alkoxide is benzyltrimethylammonium methoxide, R is methyl, and $R_1$ is hydrogen.

* * * * *